United States Patent [19]
Prince et al.

[11] Patent Number: 5,536,237
[45] Date of Patent: Jul. 16, 1996

[54] BLOOD EXTRACTION FLOW CONTROL CALIBRATION SYSTEM AND METHOD

[75] Inventors: Paul R. Prince, San Juan Capistrano; Robin Huff, Costa Mesa, both of Calif.

[73] Assignee: Baxter International Inc., Deerfield, Ill.

[21] Appl. No.: 891,527

[22] Filed: Jun. 1, 1992

[51] Int. Cl.⁶ .................................... A61M 1/03
[52] U.S. Cl. ........................ 604/4; 604/6; 128/DIG. 13
[58] Field of Search ........................ 604/4, 5, 6, 7, 604/54, 65, 66, 67, 245; 128/DIG. 13

[56] References Cited

U.S. PATENT DOCUMENTS

| | | | |
|---|---|---|---|
| 4,392,849 | 7/1983 | Petre et al. | 604/66 |
| 4,710,164 | 12/1987 | Levin et al. | 604/66 |
| 4,795,314 | 1/1989 | Prybella et al. | 604/6 X |

*Primary Examiner*—Sam Rimell
*Attorney, Agent, or Firm*—Bruce M. Canter

[57] ABSTRACT

A method and system for calibrating and controlling the withdrawal of a fluid, such as blood, from a fluid source, such as a blood vessel, includes a fluid pump, a pressure sensor, a flow rate sensor, and a microprocessor based flow control subsystem. The flow control subsystem optimizes the flow rate by sensing zero flow rate pressure within the subject, making a plurality of periodic flow path pressure measurements and extrapolating a calibration flow rate curve. A control curve is generated by utilizing the zero-flow rate pressure point, the slope of the calibration curve, and an empirically predetermined pressure. The blood pump is then operated at a maximum speed that is limited by the flow control curve to maximize flow without occlusion or collapse of the blood vessel during blood withdrawal. The method and system of the invention is particularly applicable to automated apheresis systems.

42 Claims, 5 Drawing Sheets

BLOOD EXTRACTION FLOW CONTROL CALIBRATION SYSTEM AND METHOD

BACKGROUND OF THE INVENTION

1. Field of the Invention

This invention relates to a living subject adaptive blood flow control system and more particularly to an apheresis blood flow control system which optimizes blood flow by limiting the blood flow rate in accordance with a flow control curve determined individually for each donor or patient subject from actual subject data. More particularly, this invention relates to an improved blood flow control system for controlling and optimizing the rate of blood withdrawal from a blood vessel, thereby mitigating the frequency and/or severity of occlusive interruptions (e.g. collapse of vein or collapse of tubing) in the course of blood withdrawal.

2. Discussion of the Prior Art

Blood collection systems and apheresis systems such as plasmapheresis, platelet pheresis, therapeutic plasma exchange or processing, etc. as well as other systems are known which require the extraction or reinfusion of bodily fluids from or to a living subject. In the case of a plasmapheresis system whole blood is extracted from the subject, plasma is separated from the whole blood, and an extraction product containing a higher concentration of blood cells than the whole blood is reinfused back to the subject while the separated plasma is retained and used for desired purposes. Frequently, a selected volume of saline solution or other fluids are infused into the subject to replace the volume of plasma separated from the whole blood.

To optimize utilization of processing equipment and support personnel and minimize inconvenience and discomfort to the subject, it is often desirable to remove bodily fluids as rapidly as possible. However, physiological restrictions on flow rates impose practical limitations on how fast pumping can proceed.

During extraction, if the pumping rate exceeds the flow capacity of a vein into which a phlebotomy needle or catheter is inserted, the intravenous pressure will drop below approximate atmospheric pressure and the vein sidewalls will collapse under atmospheric pressure. In the following, atmospheric pressure refers to the local extravascular pressure surrounding the vein in the location away from the pressure cuff and toward the extremities. When such collapse of the vein occurs, the blood pump must be stopped or significantly slowed until the intravenous blood flow restores the intravenous pressure to a point greater than atmospheric pressure, thus refilling the collapsed portion of the vein.

Oftentimes, when the vein collapses about the needle, the end of the needle will become compressed against the sidewall of the vein. When this happens the needle will frequently become embedded within the vein sidewall or will be sealed to the vein wall by virtue of the negative pressure within the needle and tubing that can be developed following a sudden occlusion. The needle then remains occluded, even after the previously collapsed vein has been refilled with blood. It may then become necessary to remove and reposition the needle at the expense of considerable additional time delay.

Furthermore, whenever the internal vein pressure is allowed to drop below atmospheric pressure and vein collapse occurs, increased fluid flow shear can cause platelet activation or hemolysis. Also, the needle can cause damage to the endothelial cells along the vein wall, leading to blood coagulation. This is particularly undesirable early in the processing, prior to the addition of anticoagulant, since the initiation of coagulation cascade can seriously degrade, or make useless, the desired extracorporeal blood processing.

Predicting the optimal rate at which blood may be extracted from a blood vessel is difficult because intravascular flow rates and volumes vary considerably from subject to subject. Even for a given subject, the intravascular flow rate capacity can vary considerably over a given time period. When blood is being withdrawn from a peripheral vein, (e.g. a superficial vein of the antecubital fossa), moment to moment variations in blood flow through the peripheral vein may be observed due to changes in physiological variables and/or contraction/relaxation of the muscles surrounding the blood vessel. In an effort to maintain relative continuity of blood flow through the vein it is common practice to require the donor to engage in alternate contraction/relaxation of the muscles during the blood withdrawal process—usually by squeezing an object held with the hand adjacent the withdrawal site. If, however, the donor/subject is less than diligent in squeezing the object, or if the donor only squeezes the object for intermittent periods, this may result in extreme variations in blood flow within the peripheral vein during the blood withdrawal process.

Attempting to optimize the pump blood flow rate by sensing flow path pressure adjacent the needle is uncertain because the pressure drop across the needle varies substantially with flow rate, hematocrit dependent blood viscosity and needle size parameters. It is therefore common to rely on a gravity driven flow rate far below the optimum or a pumping rate that is known to be well within the blood flow capacity of most subjects. This may be far below the optimum flow rate.

One arrangement in which a plasmapheresis system serves as a reservoir for receiving and returning bodily fluids is described in U.S. Pat. No. 4,086,924 to Latham, Jr. for "Plasmapheresis Apparatus". In this system extraction occurs under vein pressure and gravity. A multi-rate blood pump for the plasmapheresis system is accelerated or decelerated to match this flow rate. Reinfusion occurs at a predetermined rate with the blood pump set to a relatively low speed condition.

A more capable blood flow control system is disclosed in U.S. Pat. No. 4,657,529 to Prince, et al., which has been assigned to the common assignee herein, and is incorporated herein by reference. As with the present system, the system disclosed in the prior patent utilizes a programmed digital processor to regulate blood flow based on sensed fluid pressure in the flow path. The flow rate, i.e. pump speed, is regulated to achieve a maximum flow rate consistent with avoiding vein occlusions. Though the system disclosed therein provides a significant improvement over prior blood flow control systems, experience has indicated that in some instances, due to errors in the slope measurement for the control curve, it is still possible to create negative pressure in the blood vessel, resulting in vein collapse. Thus, what is needed is an improved system and method for calibrating and controlling fluid withdrawal which utilizes a more accurate slope calculation, thus extending the operating range of the system.

SUMMARY OF THE INVENTION

The present invention comprises a system for withdrawing fluid from the human body at adaptively controlled flow rates.

In accordance with a broad aspect of the invention, there is provided an improved method and system for calibrating and controlling the withdrawal of fluid from a variable source, such as a blood vessel, at an optimal rate for each subject. The flow control system may comprise a fluid reservoir fluidly connected to a blood vessel by a first fluid flow path. A pump is provided for pumping blood from the blood vessel, through the first fluid flow path to the fluid reservoir. A pressure sensor is provided for sensing pressure indications, including a zero flow pressure indication and a series of flow path pressure measurements, and a flow rate sensor is provided for sensing the flow rate within the first fluid flow path. A flow rate control system is provided to receive and process the sensed pressure and sensed flow rate indications and to generate a flow control curve which, in accordance with the sensed changes in the pressure and flow rate, modulates the provision of flow rate control signals to the pump. By obtaining a more accurate zero flow pressure measurement, and by taking a series of periodic flow path pressure measurements, a more accurate control curve is generated than was previously possible.

The control system is generally programmed and adapted to carry out the steps of the method of the present invention, and includes the following features:

(a) means for generating an indication of pressure within the subject at zero flow rate;

(b) means for generating a calibration flow rate curve comprised of a plurality of periodic flow path pressure measurements;

(c) means for generating a flow rate control curve utilizing the slope of said calibration flow rate curve, said zero flow pressure indication, and a translation from said zero flow pressure indication corresponding to a predetermined intravascular pressure value; and (d) means for generating during conditions of normal operation flow rate control signals limiting the actual flow rate to a magnitude along the flow rate control curve.

In accordance with a preferred embodiment of the invention, the calibration and control system includes a pressure cuff which is utilized to provide pressurization of the subject's flesh surrounding the blood vessel to increase the usable range of operating internal vein pressures. The pressure cuff pressure provides an indication of the maximum operating pressure due to the fact that an internal vein pressure that is higher than the cuff pressure would result in all of the blood flowing under the cuff, precluding withdrawal of some of the blood flowing into the vein.

Still further in accordance with a preferred embodiment of the invention, the calibration flow rate curve generating means includes (1) means for depressurizing the pressure cuff so that a zero flow rate pressure can be determined and (2) means for pressurizing the pressure cuff and means for rapidly and uniformly accelerating said fluid pump so that a large number of pressure measurements can be taken periodically.

Still further in accordance with a preferred embodiment of the invention, the calibration flow rate curve generating means includes means for mathematically processing the periodic flow path pressure measurements to obtain a Least-Squares slope approximation.

In another embodiment, the means for generating a flow rate curve includes means for adjusting the slope of the calibration flow rate curve to compensate for changes in internal vein pressure due to the rapid acceleration of the blood pump during the calibration period. In one embodiment, the slope adjusting means includes means for mathematically processing the periodic flow path pressure measurements to obtain a Binomial fit having a linear portion. The linear portion is then extracted to determine the slope of the control curve. Other mathematical methods of curve fitting and linear component approximation which are known to those skilled in the art can be utilized as well.

Further, in accordance with a preferred embodiment of the invention, the fluid control system includes a control panel coupled to convey operator commands to the controller. The controller includes a programmed digital processor which operates for each new subject and environment to determine zero flow vein pressure and to determine the slope of a subject dependent control curve based upon the generated calibration flow rate curve. The control curve which is generated is within the substantially linear flow rate capacity of the subject and is generated from the zero flow pressure point, the calibration flow rate curve, and an empirically predetermined pressure offset. The controller then commands the fluid pump to maintain the system at a desired maximum nominal flow rate subject to any limitations imposed by the flow rate control curve.

In a preferred embodiment, the digital processor operates on discrete (e.g. 50 msec) computer cycles. Such computer cycles periodically update flow rate commands to the pump. During each computer cycle the processor (a) samples the sensed pressure, (b) provides atmospheric calibration therefor and, then, (c) provides stability compensation to generate a compensated pressure value. The actual flow rate is also calculated and updated in response to a pump motor velocity count signal and then used to find the pressure intersection point on the control curve at the actual flow rate. The actual sensed pressure is subtracted from the control curve intersection pressure point to produce a pressure error value.

The pressure error signal is then integrated and scaled to produce a flow control command. The integrator is subjected to a lower limit of zero, an upper limit equivalent to the maximum flow rate, and a rate of change limit to produce an adjusted flow control command which is applied as a flow rate command to a digital feedback flow rate control servo loop.

A forward portion of the servo loop includes a flow rate error integrator, a scaler and a D-A converter coupled to apply an integrated flow rate error signal to a pulse width modulated (pwm) motor control system which is itself a servo loop and drives the pump motor. A velocity signal from the pump motor is provided as feedback to the pwm motor control system and through a stability compensating calculation to provide the updated flow rate values which are used in accessing the flow rate limit curve and in determining the flow rate error signal in the flow rate servo loop. Actual flow rates and actual pressures contain scaling errors due to tubing geometry and hardness, and pressure sensor scale errors. However, since the system adapts by measuring all calibration points with substantially the same scaling errors as are experienced at other flow rates and corresponding pressures, these errors are substantially eliminated, to the extent that the scaling errors are constant linear functions. That is, the system operates in its own flow and pressure units which are determined by the instant tubing and pressure sensor involved. Compensating corrections for pump or tubing nonlinearity may also be provided for large negative pressures wherein the polyvinylchloride tubing, which has a relatively low hardness, tends to flatten somewhat within the peristaltic roller pump and therein exhibits a correspondingly somewhat reduced flow rate than that which is calculated from an ideal linear extrapolation of data measured at lower magnitude negative pressures.

Other control systems and methods, which are known to those skilled in the art, can be utilized for operating the fluid withdrawal system in accordance with the requirements of the control curve generated by the invention.

It is thus an object of the present invention to provide an improved system and method for calibrating and controlling the withdrawal of fluid from a blood vessel by generating and utilizing an improved flow control curve to maximize fluid withdrawal without occlusion or collapse of the blood vessel.

BRIEF DESCRIPTION OF THE DRAWINGS

A better understanding of the invention can be had from a consideration of the following detailed description, taken in conjunction with the accompanying drawings in which.

DETAILED DESCRIPTION OF THE ILLUSTRATIVE EMBODIMENT

The detailed description set forth below in connection with the appended drawings is intended merely as a description of an illustrative embodiment of the invention, and is not intended to represent the only form in which the present invention may be constructed or utilized. The description sets forth the functions and sequence of steps for construction and implementation of the invention in connection with the accompanying figures. It is to be understood, however, that the same or equivalent functions and sequences may be accomplished by different embodiments that are also intended to be encompassed within the spirit and scope of the invention.

Figure 1:
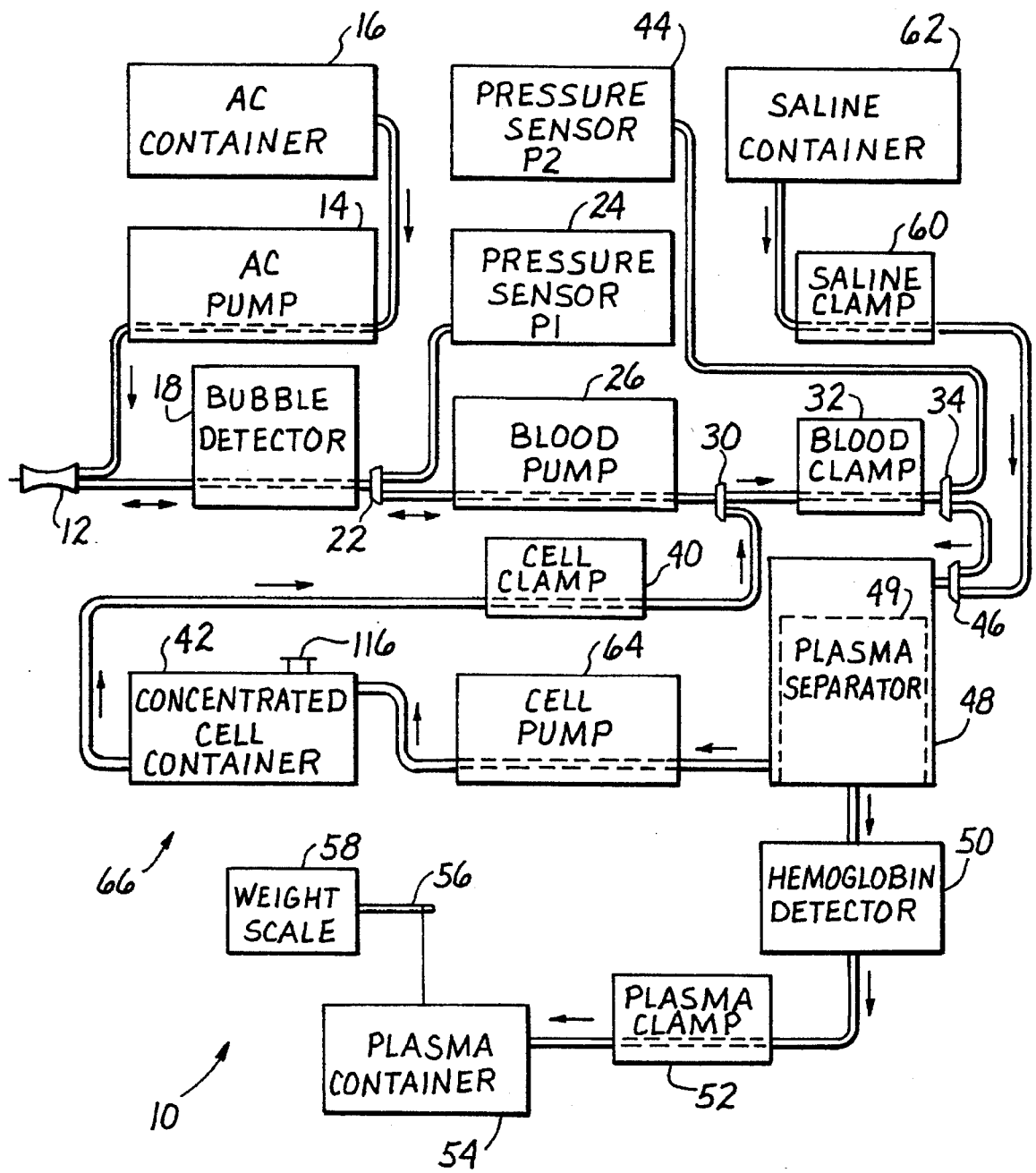
FIG. 1 is a schematic and block diagram representation of a fluid flow path for a plasmapheresis system using an adaptive body fluid flow control system in accordance with the invention.

Referring now to FIG. 1, there is illustrated a noninvasive, sterile plasmapheresis flow path 10 for a plasmapheresis system utilizing an adaptive bodily fluid flow control system in accordance with the invention. Intravenous connection of the flow path 10 to a subject is provided by a bodily fluid flow channel connection such as a phlebotomy needle 12 which is suitable for insertion into a vein of a subject to provide communication of blood and/or other fluids between the subject and the flow path 10 of the plasmapheresis system.

The flow path branches immediately adjacent the needle 12 with one branch extending through a noninvasive peristaltic anticoagulant pump 14 to an anticoagulant container 16. During a whole blood extraction cycle the anticoagulant pump 14 operates to supply and mix a small percentage of anticoagulant with the blood as it is being extracted to prevent activation of clotting mechanisms to prevent clotting and clinging of the blood to tubing sidewalls as it passes through the flow path 10. By mixing the anticoagulant with the whole blood at the needle 12 during extraction, the two fluids become fully mixed and less anticoagulant is required. This is a desirable effect which helps minimize the amount of anticoagulant in the separated plasma.

The other branch of the blood flow path 10 extends through a bubble detector 18 to another branch point 22. From branch point 22 one branch extends to a P1 pressure sensor 24 coupled to sense fluid pressure on the subject side of a blood pump 26. The pressure sensor 24 includes a disposable filter coupling the sensor to a pressure sensor tube 28 so as to maintain a noninvaded sterile atmosphere within the flow path 10. The second branch from branch point 22 extends through the noninvasive, peristaltic blood pump 26 to a branch point 30.

From branch point 30, one branch extends through a blood clamp 32 to another branch point 34. The other flow path at branch point 30 extends through a cell clamp 40 to the bottom of a concentrated cell container 42 which receives, and temporarily stores pending reinfusion, high hematocrit blood after a substantial portion of the plasma has been separated therefrom.

From branch point 34, one path extends to a second, P2 pressure sensor 44 while the other path extends through a branch point 46 to a plasma separator 48 which encloses a filter 49.

While the exact nature of the plasma separator 48 is not material to the present invention and can be fully conventional if desired, a highly advantageous plasma separator is a rotating filter type of separator as illustrated in application Ser. No. 591,925 filed Mar. 21, 1984 for "Method and Apparatus for Separation of Matter From Suspension" by Donald W. Schoendorfer. For this type of separator the end product plasma output is coupled through a hemoglobin detector 50 and a plasma clamp 52 to a plasma container 54 which is maintained at atmospheric pressure. The plasma container 54 is suspended from a tension arm 56 to a weight scale 58 which provides feedback to the plasmapheresis system of the amount of plasma within container 54. Since P2 pressure sensor 44 is coupled to the inlet of plasma separator 48 and since the plasma outlet of separator 48 is maintained at atmospheric pressure plus a small adjustment for vertical height differences, the pressure sensor P2 44 provides an indication of transmembrane pressure for the filter membrane within plasma separator 48. This transmembrane pressure indication can be useful in monitoring and controlling the operation of plasma separator 48.

Another flow path from branch point 46 extends through a saline clamp 60 to a saline container 62. This flow path enables the separator to be initially primed with a small amount of saline prior to initial use, to be cleansed with saline after final use, and provides a flow path of saline solution from the saline container 62 through branch point 46 to branch point 34 and then through blood clamp 32 to blood pump 26 and bubble detector 18 to phlebotomy needle 12. This path enables saline solution to be communicated to the subject at the end of a plasmapheresis operation to provide fluid replacement of any plasma removed from the whole blood of the subject.

A cell pump 64 is coupled between an outlet of plasma separator 48 on the same side of the membrane as the inlet at the top of concentrated cell container 42. Cell pump 64 thus controls the flow of high hematocrit blood from plasma separator 48 to concentrated cell container 42 where the high hematocrit blood is temporarily stored during an extraction subcycle. Whenever the concentrated cell container 42 becomes full, a reinfusion subcycle is executed in which cell clamp 40 is opened, blood clamp 32 is closed, and blood pump 26 is operated in the reverse direction to transfer the high hematocrit blood from concentrated cell container 42 back to the subject through bubble detector 18 and phlebotomy needle 12.

The entire bodily fluid flow path 10 including all of the branch points 22, 30, 34, 46 and the interconnecting tubing 66 are comprised of inexpensive, disposable materials which may be presterilized. The blood flow path is maintained completely noninvasive so as to protect against contamination and prevent and maintain sterility of the bodily fluids. The non-hardware portion of the flow path may be fully replaced for each different subject. Even the plasma separator 48 may be constructed such that only a sterile, disposable, portion comes into contact with the bodily fluids. The risk of transmitting disease to the subject during the plasmapheresis operation is thereby minimized.

In order to optimize use of the plasmapheresis equipment and maintenance personnel while minimizing inconvenience and discomfort to the donor subject, it is desirable to accomplish a plasmapheresis procedure as rapidly as possible. Typically, the factor which limits the plasmapheresis operating rate is the intravenous blood volume and/or intravenous flow rate within the blood vessel from which blood is being extracted and/or into which blood is being infused. It is desirable to continually attempt to withdraw blood from the blood vessel at a relatively fast rate (e.g. 150 ml/min.) and, indeed, experience has taught that many human subjects are able to withstand and support consistent withdrawal and/or infusion of fluids at such relatively high rate (e.g. 150 ml/min.) without any incidence of vein collapse or regional depletion of available intravascular volume. However, even when momentary depletion or diminution in the available intravascular volume is observed, it is desirable to effect short term downward adjustments or pauses in the withdrawal rate, but thereafter, to once again attempt to increase the withdrawal rate toward a predetermined maximum (e.g. 150 ml/min.) so as to effectively challenge the system and the donor to accomplish the withdrawal at the fastest possible rate for that particular human subject, under the then present conditions.

The adaptive blood flow control system of the present invention is operable to determine the maximum available flow rate for extraction and to control the operation of the blood pump 26 such that the blood pump will operate either at a reduced maximum rate (e.g. less than 150 ml/min.) or at a preset maximal flow rate (e.g. 150 ml/min.) if the donor subject can accommodate such preset maximum rate.

It should be emphasized that the system can be utilized to calibrate and control the infusion or reinfusion of blood into the subject according to the same principles as outlined herein for extraction and someone skilled in the art would be able to utilize the system and method disclosed herein for that purpose as well.

A vein supplying or receiving intravenous bodily fluids through the phlebotomy needle 12 can be analogized to a small diameter, thin walled, rubber tube. Normally, the body maintains a pressure within the vein of approximately 10 mmHg above atmospheric. This is sufficient to maintain the vein expanded and permit normal blood flow. However, if blood is extracted faster than it can be supplied by the vein, the pressure within the vein drops toward atmospheric, causing the external atmospheric pressure against the body to collapse the vein. Blood flow can be reinstated by terminating pumping through the needle until the depleted blood volume is replaced and normal vein pressure is restored within the vein. However, frequently the sidewalls of the vein engage the end point of the phlebotomy needle as the vein collapses to thereby occlude blood flow through the needle. Even as the vein reexpands, the needle may remain occluded against the vein wall and it then becomes necessary to reposition the needle. This of course imposes considerable time delay and may cause donor anxiety. Clotting processes may be initiated due to high blood shear and occlusion of the needle against the vein wall may cause endothelial cell damage.

During venepuncture it is common to place a pressure cuff around the upper portion of the subject's arm with a pressure of about 60 mmhg to make pressurize the vessel. In the prior art system disclosed in U.S. Pat. No. 4,657,529 to Prince, et al., the goal of the system is to insure that the internal vein pressure is maintained between atmospheric pressure and the inflation pressure of the pressure cuff. If the internal vein pressure drops below atmospheric pressure, the vein will collapse. If, on the other hand, the internal vein pressure exceeds the inflation pressure of the pressure cuff, then the blood will pass under the cuff and not be removed. Thus, if the internal vein pressure is maintained within this range, the vein will not collapse, and substantially all of the blood entering the vein will be removed.

To maintain the internal vein pressure within the acceptable range, it is necessary to obtain an accurate indication of the zero-flow pressure inside the vein, and to determine the linear relationship between blood flow and the pressure drop across the needle. With this information, the actual pressure inside the vein can be calculated continuously for all flow rates, and can be maintained within the bounds of atmospheric pressure and pressure cuff pressure.

Figure 2:
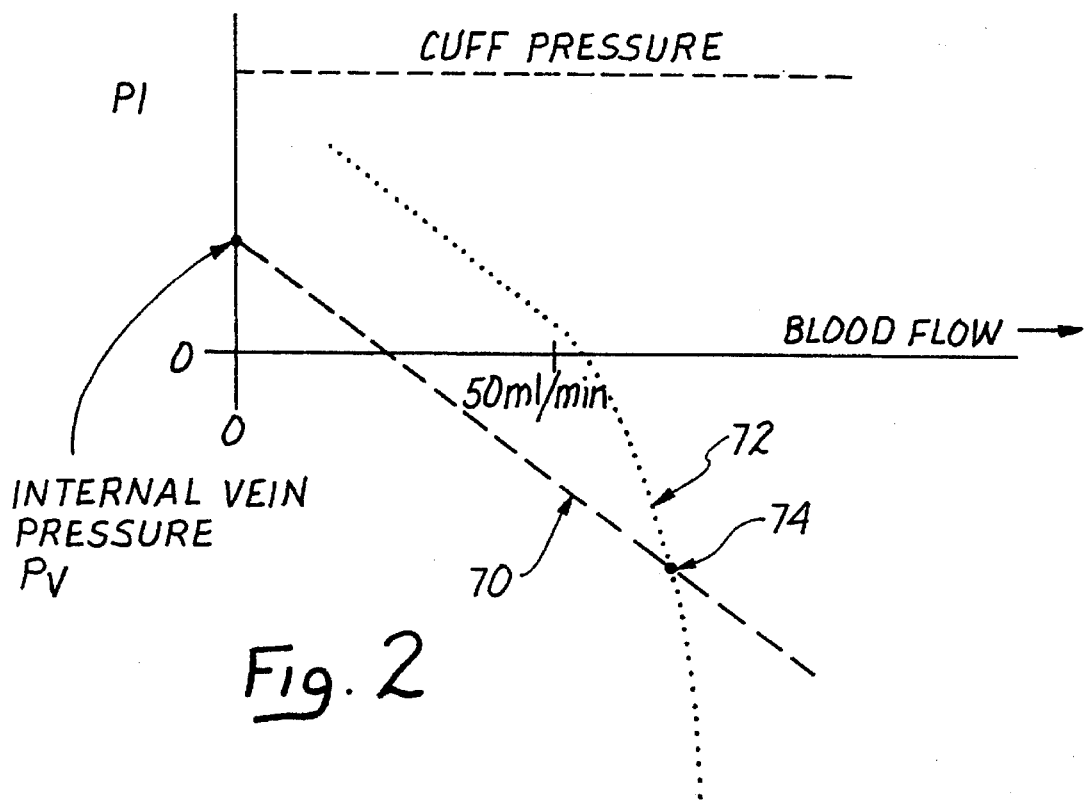
FIG. 2 is a graphical illustration of a dynamic pressure-flow curve having an operating point that intersects an actual pressure-flow curve.

In general, whenever blood is flowing through needle 12 within a vein, the pressure sensed at pressure sensor 24 is the sum of the internal vein pressure and the negative pressure drop across the needle, assuming a negligible pressure drop within the tube set or in the vein near needle 12. This is illustrated in FIG. 2, where internal vein pressure at zero blood flow is shown at point Pv. As blood flow increases and the negative pressure drop across the needle adds to P1, the value of P1 pressure continuously decreases in a linear fashion as illustrated by needle/blood pressure characteristic curve 70. As measured at pressure sensor 24, the actual sensed pressure will follow a curve 72, which if continued will approach atmospheric pressure inside the vein, causing vein collapse. Thus, it is possible, in principle, to obtain an operating point 74 from the intersection of the sensed pressure curve 72 with pressure characteristic curve 70. If Pv is in fact the appropriate internal vein pressure, then operating point 74 will insure that the system operates within the acceptable parameters.

Figure 3:
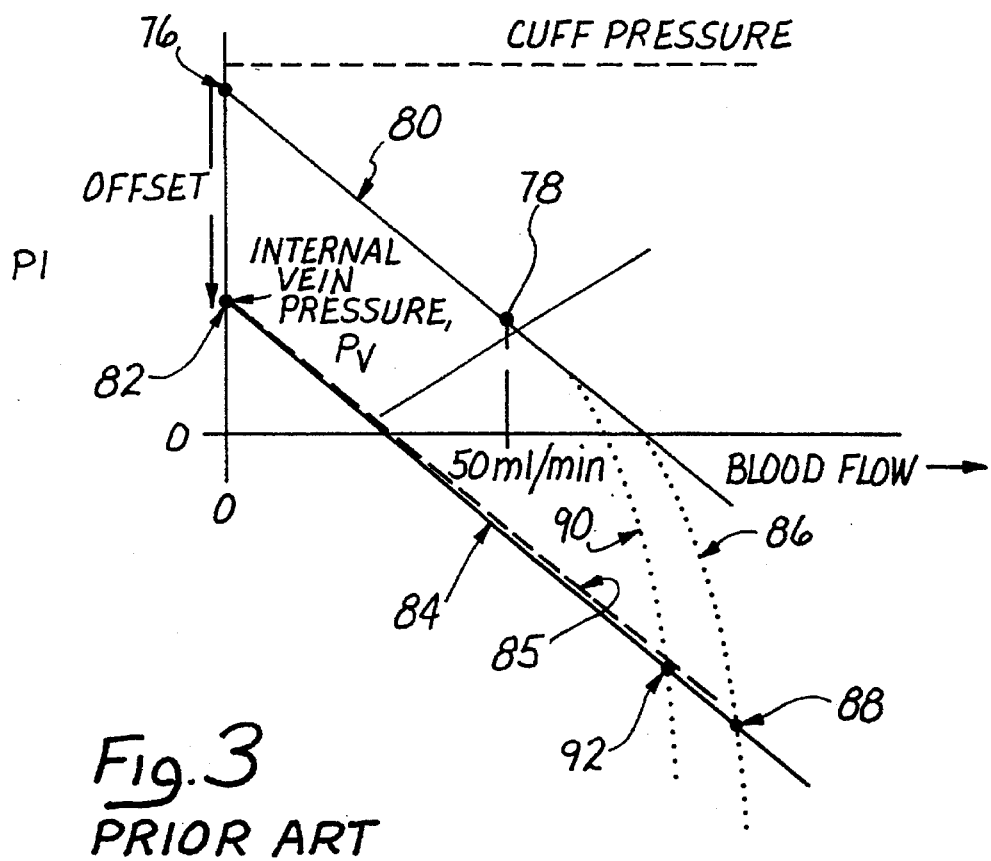
FIG. 3 is a graphical illustration of the control curve generated in prior art control system.

In the prior art system of Prince, et al. during extraction the pressure within the cuff is reduced to about 40 mmHg. Thus, the zero-flow rate (through needle 12) internal vein pressure is determined largely by the cuff pressure during extraction and is approximately 24–40 mmHg The determination of the linear pressure-flow relationship in this system is illustrated in FIG. 3. In order to determine the flow characteristics of the needle and blood combination, the pressure at two flow points between the needle 12 and blood pump 26 is measured. The first point is the zero-flow rate point 76, which we have determined will occur, approximately, at the pressure cuff pressure. The second point 78 is at 50 ml/min, which is expected to be well within the flow rate capability of the subject. From points 76 and 78 a linear calibration flow rate curve 80 is generated. The linear calibration flow rate curve 80 is then translated downward by an amount equal to a difference in pressure between the 40 mmHg pressure at the zero-flow rate point 76 and a minimum acceptable internal vein pressure, such as 4 mmHg, at point 82, to generate a translated control curve 84, coextensive with the actual needle/blood pressure characteristic curve 85, which is represented by a dashed line.

As disclosed in Prince, et al., alternate control curves can be generated for subject donors of low blood flow capability or subject donors with small veins. These alternate curves are generated by rotation of control curve 84. Prince, et al, further discloses the development of an error signal, after calibration, between control curve 84 and the measured pressure during operation. The error signal is processed and used in a closed loop feedback control system to stabilize pump 26 at a flow rate along control curve 84.

FIG. 3 shows the operation of the system for two different internal vein blood flows, Q1 and Q2. Q1 has its corresponding sensed pressure curve 86 which intersects control curve 84 at operating point 88 and Q2 has its corresponding sensed pressure curve 90 which intersects control curve 84 at operating point 92.

It is important to appreciate that stabilizing blood flow anywhere along control curve 84 results in the internal vein pressure Pv at point 82. This is because the slope of control curve 84 is identical to the slope of the pressure characteristic curve 85. That is to say, the linear needle/blood flow relationship, demonstrated by pressure characteristic curve 85, allows an extrapolation back to the zero-flow point 82. This is due to the fact that at point 82 there is no pressure drop across the needle, which acts as a pressure monitor within the vein. However, the internal vein pressure Pv will only coincide with the end point of control curve 84 if the slope of control curve 84 is equal to the slope of the pressure characteristic curve 85.

Since the goal of the system is to maintain internal vein pressure Pv comfortably above atmospheric pressure (zero on the pressure axis) and comfortably below cuff pressure (usually 40 mmhg), it is essential that the slope of the pressure characteristic curve 80 and the pressure offset be accurately determined. If there is an error in the slope measurement, then internal vein pressure point Pv will not reside at the endpoint of control curve 84, since the control curve slope will not accurately reflect the slope of the pressure characteristic curve 80.

Figure 4:
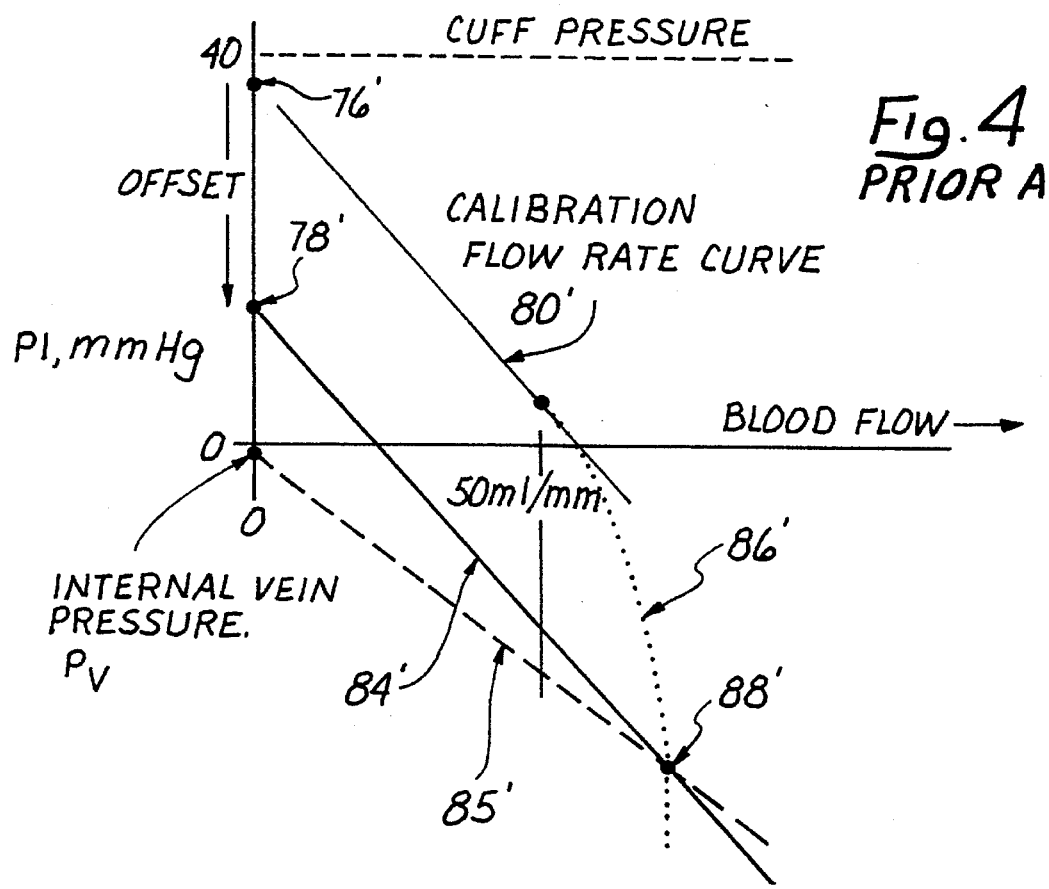
FIG. 4 is a graphical illustration of an erroneous control curve generated in a prior art control system.

FIG. 4 illustrates a control curve 84' which was generated from two points according to the prior art system. Points 76' and 78' constitute errors resulting in control curve 84' having a slope that is steeper than the actual needle/blood flow relationship which is exemplified by the actual pressure characteristic curve 85'.

In the prior art system, the generated control curve 84' is used to increase blood flow until the corresponding sensed pressure curve 86' intersects control curve 84' at operating point 88' to satisfy the feedback system. Extrapolating back from this intersection point 88' along actual pressure characteristic curve 85' indicates that the internal vein pressure point Pv is negative, resulting in vein collapse. Thus, large errors in slope determination are detrimental to the operation of the system.

It is also the case that errors in the calculation of the zero-flow pressure measurement, point 76' in FIG. 4, result in errors in the offset pressure point 82'. This contributes to operational degradations such as vein occlusion if point 82' is too low, or insufficient blood flow withdrawal if point 82' is too high. Similarly, at point 78' there is a variation in the pressure value at the time point 78' is recorded, depending upon how close extraction flow (Qdraw) is to internal vein blood flow (Qin).

Figure 5:
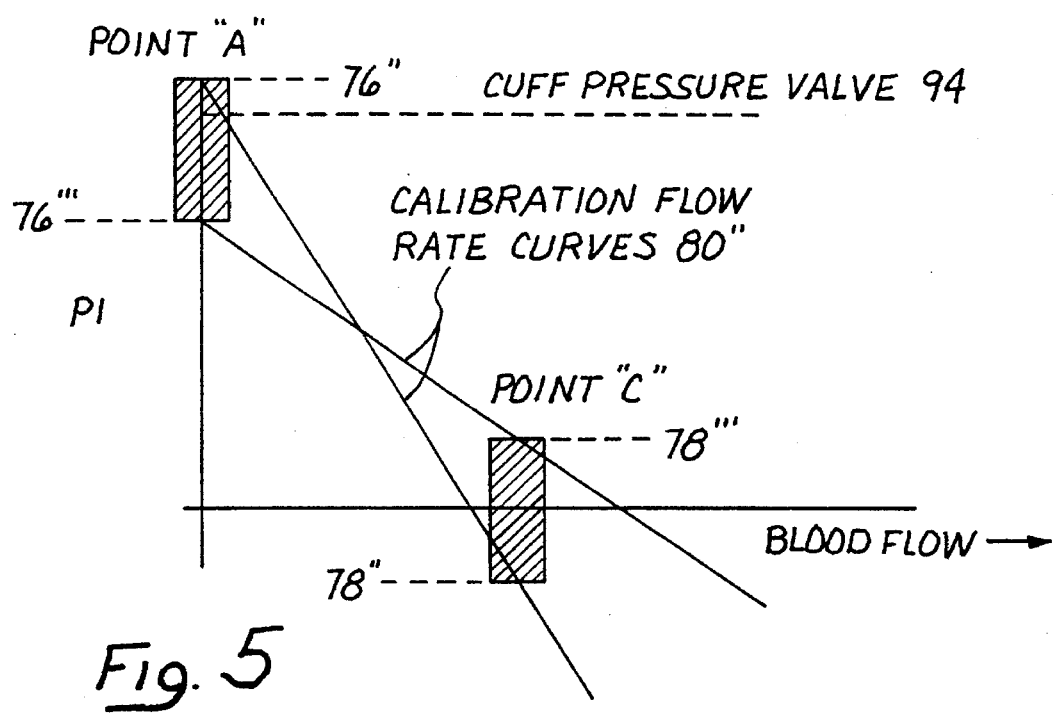
FIG. 5 is a graphical illustration of variations in the slope of the control curve in a prior art control system.

FIG. 5 illustrates how variations in measured points A and C can result in wide variations in linear calibration flow rate curves 80". In the prior art method, the slope of the control curve is determined by taking a zero-flow calibration pressure value (point A) and a pressure value when the fluid draw is assumed to be less than Qin (Point C).

If Qin is very high, such as 180 ml/min, then when the drawn blood Qdraw is zero, resulting in a high zero-flow pressure point 76", pressure within the vein may become somewhat higher than the pressure cuff pressure value 94. This is due to the fact that a driving force is required to push the high blood flow through the venous regions compressed by the pressure cuff. At the point C measurement, high input vein flow Qin produces a relatively high value point 78'''.

On the other hand, if Qin is very small, such as 55 ml/min, then the pressure within the vein may be substantially lower. In fact, since the pressure cuff is not infinitely long, edge effects cause the cuff's influence within the arm to be less than the pressure 94 within the pressure cuff, as illustrated by pressure points 76''' and 78".

Thus, depending upon how close Qdraw is to Qin, there is a variation in the pressure value at the time points A and C are recorded, as shown by points 76" and 76''' and points 78" and 78''', respectively. These variables can cause significant variations in the actual pressure measured for points A and C, from donor to donor and from cycle to cycle.

These variations in points A and C will result in large variations in the slope of the calibration flow rate curve as well as in the offset location of control curve 84. Consequently, these variations will result in inappropriate control curves.

Figure 6:
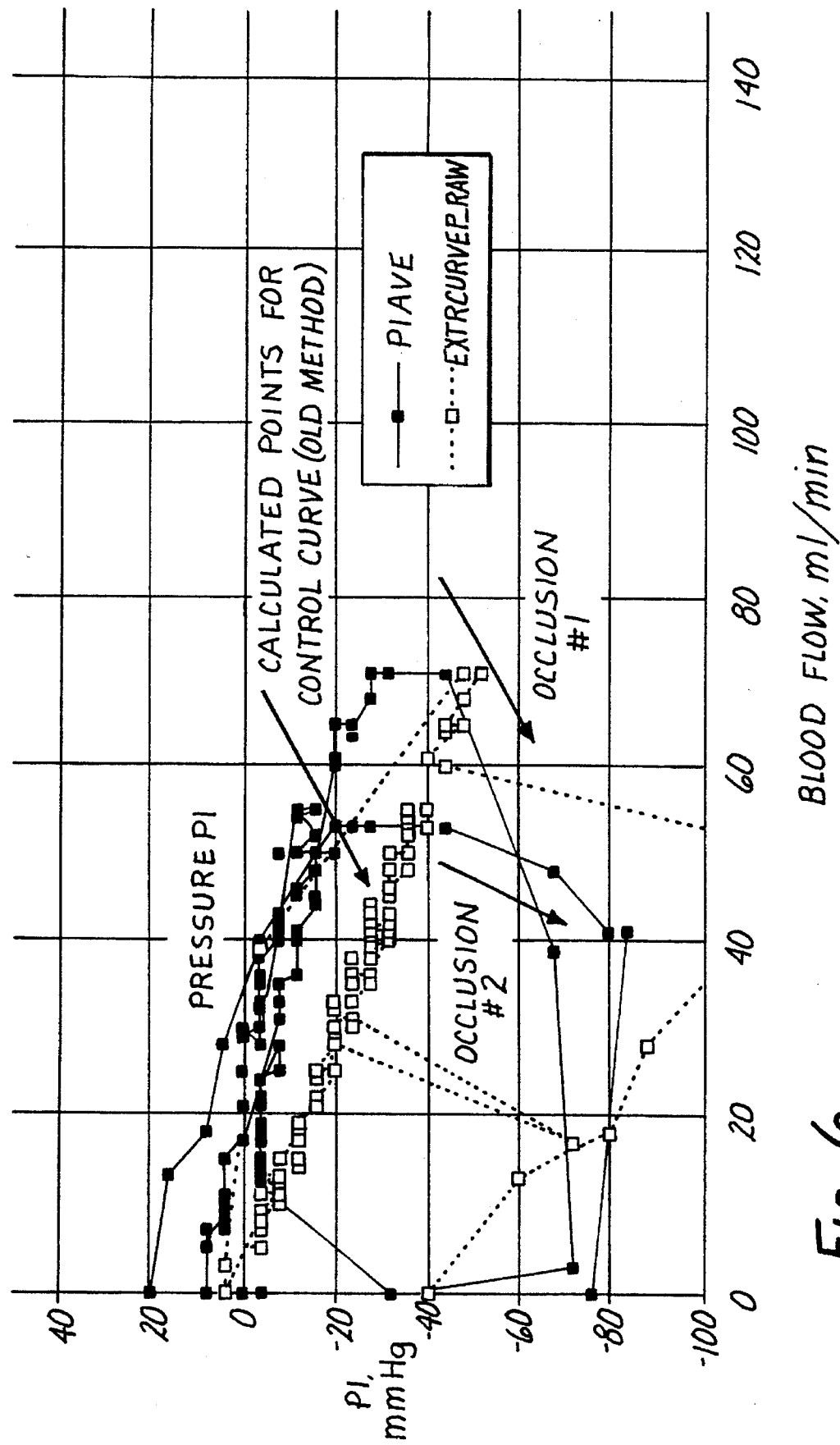
FIG. 6 is a graphical illustration of donor extraction data in a prior art control system.

In FIG. 6, actual data is plotted showing P1 pressure versus blood flow using the prior art control curve calibration system. In this case, the slope of the needle/blood flow characteristics was incorrectly measured, and is too steep. The trajectory of the two occlusions is seen where the pressure rapidly goes negative, followed by a rapid reduction of blood flow. The data points are taken one second apart.

In order to generate a more accurate control curve, for example in wide-range uses such as 30 ml/min to 150 ml/min extraction control systems, it is imperative that the zero-flow pressure measurement and the needle/blood pressure-flow relationship be more accurately established.

Figure 7:
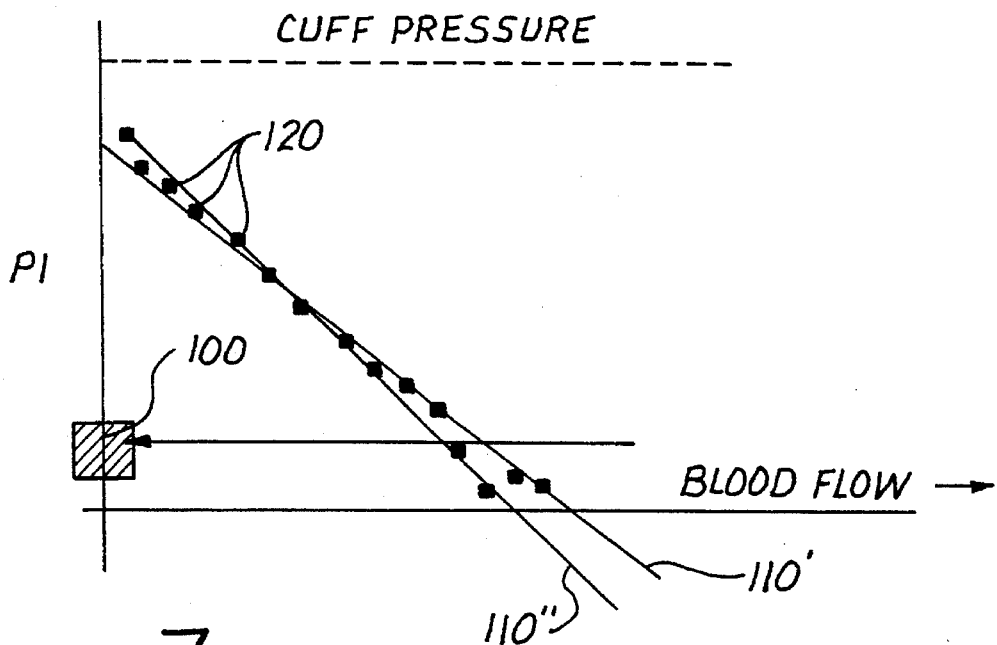
FIG. 7 is a graphical illustration of the calibration flow rate curve and zero-flow pressure measurement in accordance with the invention.
Figure 8:
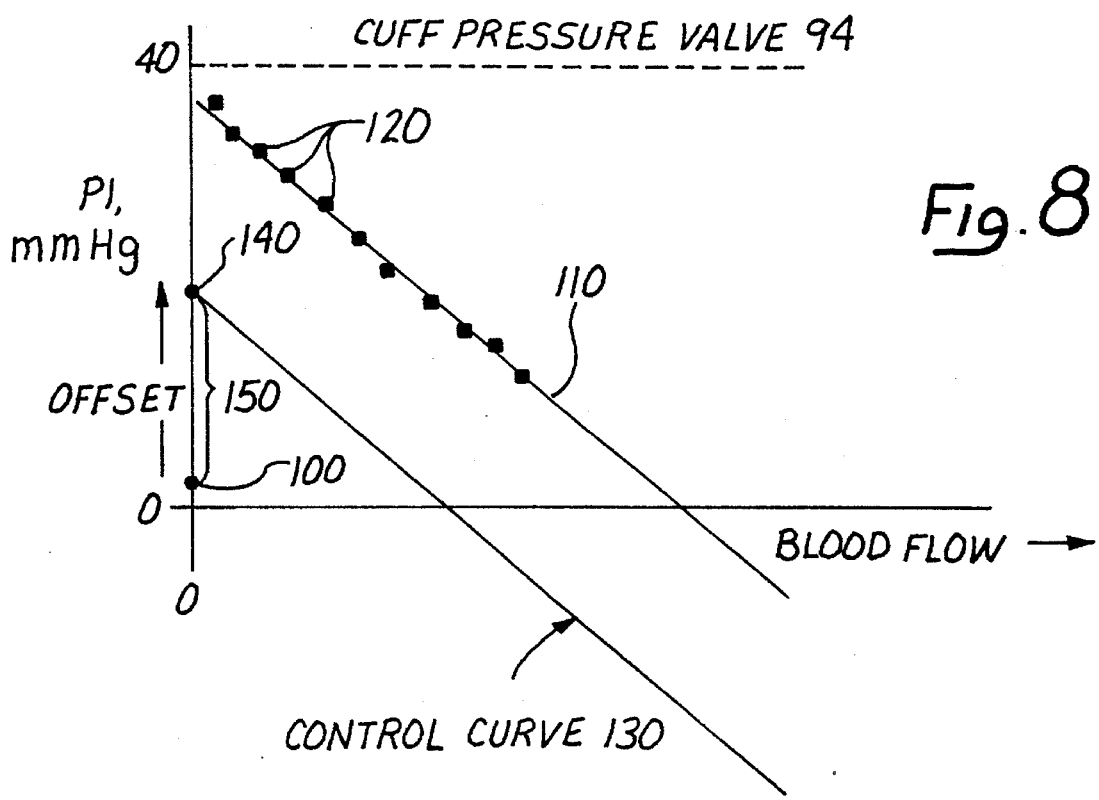
FIG. 8 is a graphical illustration of an extraction flow rate control curve in accordance with the invention.

The method of generating a more accurate control curve in accordance with the invention is illustrated in FIGS. 7 and 8. Calibration is improved in two ways: (1) zero-flow pressure point 100 is measured without the uncertainties introduced when the pressure cuff is pressurized, and (2) the needle/blood pressure flow-relationship is measured quickly at many points, while the internal vein pressure does not have time to change significantly, providing improved accuracy in the slope of linear calibration flow rate curve 110.

Prior to the initiation of calibration blood draw, the pressure cuff is deflated. Typically, the venous pressure stabilizes within a few seconds to a more repeatable range than when the cuff is inflated. With the cuff inflated, the time constant of pressure stabilization is often twenty seconds or more whereas it is about three seconds with the cuff deflated.

Thus, a more accurate zero-flow, internal vein pressure measurement is obtained quickly. The deflated cuff zero-flow pressure measurement point includes any gravitational offset involved that is a function of the donor chair height. Hereafter, this measurement will be termed the zero flow point.

After the zero-flow point is obtained, the cuff is pressurized and the vein pressure is allowed to stabilize. Blood pump 26 is accelerated reasonably rapidly and uniformly and a large number of pressure measurements 120 are taken periodically. For example, 160 values may be taken over an eight second acceleration of the blood pump. These pressure and blood flow values are fitted to a pressure-flow acceleration curve 110 which is assumed to have a constant internal vein pressure during pump acceleration. FIG. 7 illustrates two such calibration curves 110' and 110", which could be derived from the data points 120. It should be noted that the possible variations between curves 110' and 110" are not very significant.

In a preferred embodiment the pressure and blood flow values 120 are mathematically processed to obtain a Least-Squares slope estimation. In another embodiment a Binomial Fit of data points 120 can be utilized with the linear portion extracted to determine the slope. This method will permit correction of the slope estimation to reflect changes in internal vein pressure that occur during the calibration period. Other mathematical methods of curve fitting which are known to those skilled in the art can be utilized as well.

In another preferred embodiment, the blood pump may be first accelerated to a peak value such as 30 ml/min and then decelerated back to 0 ml/min and pressure-flow values may be taken over the acceleration and deceleration in order to compensate for changes in the internal vein pressure during the calibration period.

FIG. 8 illustrates the generation of the control curve 130 in accordance with a preferred embodiment of the invention. The control curve zero intercept point 140 is established above point 100 by an empirically determined pressure offset value 150, which, in a preferred embodiment, is a fraction of a maximum operable internal vein pressure. The pressure offset value 150 is determined by taking into consideration variations in the zero-flow point and variations in the maximum operable vein pressure from subject to subject. These variations are used to provide a typical operating vein pressure range within which a comfortable margin can be obtained. This pressure range is between atmospheric pressure and the pressure cuff pressure. Thus a pressure offset is constructed which is comfortably above zero-flow point 100 while still allowing for small dynamic variations above and below control curve 130.

In a preferred embodiment, pressure offset value 150 is between the deflated cuff zero-flow point 100 and cuff pressure value 94. In a preferred embodiment, pressure offset 150 is a fraction of the cuff pressure value 94 above the zero-flow point 110, such as one-quarter of cuff pressure value 94. Thus, a control curve 130 is utilized which has an endpoint 140 that is between zero-flow point 100 and cuff pressure value 94. This insures that the internal vein pressure is maintained below cuff pressure 94, permitting substantially total blood withdrawal, and above the zero-flow point, preventing vein occlusion.

While what has been shown and described above is an adaptive calibration and control system which is particularly useful for controlling bodily fluid flow rates in a plasmapheresis system for the purpose of enabling a person of ordinary skill in the art to make and use the invention, the invention is not limited thereto. It will be appreciated that the principles disclosed herein have a broader applicability then has been discussed, such as larger vein use, higher blood flow, and for use with other means of extracting blood, such as catheters and arterial shunts. Accordingly, any modifications, variations or equivalent arrangements within the scope of the attached claims should be considered to be within the scope of the invention.

What is claimed is:

1. A system for calibrating the control of the flow of fluid in a given direction to or from a subject having a limited flow rate accommodation comprising:

a pressure cuff coupled to the subject to provide pressurization of the subject's blood vessel to increase the dynamic range of operating internal vein pressures;

a fluid pump that is connectable in fluid pumping relationship along a fluid flow path between the subject and a fluid processor or reservoir;

pressure sensing means coupled to sense fluid pressure in the fluid flow path between the fluid pump and the subject and generate indications of the sensed pressure;

a flow rate sensor coupled to provide an indications of fluid flow rates along the first fluid flow path; and a fluid pump control system coupled to receive the sensed pressure and flow rate indications and provide to the fluid pump flow rate control signals in response thereto, the fluid pump control system including:

(a) means for inflating and deflating the pressure cuff;

(b) means for generating a zero-flow point, including means for sensing the internal fluid pressure within the subject's blood pressure at a zero flow rate while the pressure cuff is deflated, said zero flow point being an indication of pressure within the subject at zero flow rate;

(c) means for making periodic flow path pressure measurements while the pressure cuff is inflated and means for generating a calibration flow rate curve comprised of the plurality of periodic flow path pressure measurements;

(d) means for generating a flow rate control curve utilizing the slope of said calibration flow rate curve, said zero-flow point, and a translation from said zero-flow point corresponding to a predetermined intravascular pressure value; and (e) means for generating control signals limiting the actual flow rate to a magnitude along the flow rate control curve.

2. The system of claim 1 wherein the predetermined pressure value is empirically determined by taking into consideration variations in zero-flow vein pressure and variations in the maximum operable vein pressure from subject to subject.

3. The system of claim 1 wherein the predetermined pressure value is a fraction of a maximum operable pressure.

4. The system of claim 1 wherein said means for generating a calibration flow rate curve includes means for pressurizing said pressure cuff and means for rapidly and uniformly accelerating said fluid pump so that a plurality of pressure measurements can be taken periodically.

5. The system of claim 1 wherein said means for generating a calibration flow rate curve includes means for pressurizing said pressure cuff and means for rapidly and uniformly accelerating and decelerating said fluid pump so that a plurality of pressure measurements can be taken periodically.

6. The system of claim 1 wherein the predetermined pressure value is between the zero-flow point value and the cuff pressure value.

7. The system of claim 6 wherein the predetermined pressure value is a fraction of the cuff pressure.

8. The system of claim 7 wherein the predetermined pressure value is one-quarter the cuff pressure.

9. The system of claim 1 wherein said means for generating a calibration flow rate curve includes means for mathematically processing the periodic flow path pressure measurements to obtain a Least-Squares slope estimation.

10. The system of claim 1 wherein said means for generating a calibration flow rate curve includes means for adjusting the slope of said calibration flow rate curve to correct for changes in internal vein pressure during the calibration period.

11. The system of claim 1 wherein said means for generating a calibration flow rate curve include means for mathematically processing the periodic flow path pressure measurements to obtain a Binomial fit having a linear portion attributable to the slope.

12. The system of claim 1 wherein said means for inflating and deflating the pressure cuff further comprises means for inflating the pressure cuff to pressurize the subject's blood vessel prior to venipuncture.

13. A method of controlling a flow rate of a bodily fluid along a flow path between a subject and a processor or reservoir comprising the steps of:

placing a deflated pressure cuff on the subject;

sensing the internal fluid pressure within the subject's blood vessel at zero flow rate while the pressure cuff is deflated and generating a zero-flow pressure point;

inflating the pressure cuff, waiting until the vein pressure stabilizes, initiating a blood draw, and making a plurality of periodic flow path pressure measurements;

using the flow path pressure measurements to generate a calibration flow rate curve;

generating a flow rate control curve utilizing the slope of said calibration flow rate curve, said zero-flow pressure point, and a translation from said zero-flow pressure point corresponding to a predetermined intravascular pressure value; and generating during conditions of normal operation flow rate control signals limiting the actual flow rate to a magnitude along the flow rate control curve.

14. The method of controlling according to claim 13 wherein the step of sensing the internal fluid pressure includes adjusting for gravitational effects due to the position of the donor.

15. The method of controlling according to claim 13 wherein the step of making periodic flow path measurements includes the step of rapidly and uniformly accelerating pumping of the fluid from the subject so that a plurality of pressure measurements can be taken periodically.

16. The method of controlling according to claim 13 wherein the step of generating a calibration flow rate curve includes the step of mathematically processing the periodic flow path pressure measurements to obtain a Least-Squares slope estimation.

17. The method of controlling according to claim 13 wherein the step of generating a flow rate control curve includes the step of adjusting the slope of said calibration flow rate curve to reflect changes in internal vein pressure during the calibration period.

18. The method of controlling according to claim 13 wherein the step of using flow path measurements to generate a calibration flow rate curve includes the step of mathematically processing the periodic flow path pressure measurements to obtain a Binomial fit having a linear portion attributable to the slope of said calibration flow rate curve.

19. The method of controlling according to claim 13 wherein the step of generating a flow rate control curve includes the step of empirically determining a pressure offset value by taking into consideration variations in zero-flow vein pressure and variations in the maximum operable vein pressure from subject to subject.

20. The method of controlling according to claim 13 wherein the step of generating a control curve includes the step of utilizing a predetermined pressure offset that is between the zero-flow rate pressure point and a maximum operable value.

21. The method of controlling according to claim 20 wherein the step of generating a control curve includes that step of utilizing a predetermined pressure offset that is a fraction of a maximum operable value.

22. The method of controlling according to claim 21 wherein the step of generating a control curve includes that step of utilizing a predetermined pressure offset that is one-quarter of a maximum operable value.

23. The method of controlling according to claim 13 wherein the step of making periodic flow path measurements includes the steps of pressurizing the pressure cuff and rapidly and uniformly accelerating the pumping of fluid from the subject so that a plurality of pressure measurements can be taken rapidly.

24. The method of controlling according to claim 13 wherein the step of making periodic flow path measurements includes the steps of pressurizing the pressure cuff and rapidly and uniformly accelerating and decelerating the pumping of fluid from the subject so that a plurality of pressure measurements can be taken rapidly.

25. The method of controlling according to claim 13 wherein the step of generating a calibration flow rate curve includes the step of mathematically processing the periodic flow path pressure measurements to obtain a Least-Squares slope estimation.

26. The method of controlling according to claim 13 wherein the step of generating a calibration flow rate curve includes the step of generating a slope for said calibration flow rate curve which reflects changes in internal vein pressure during the calibration period.

27. The method of controlling according to claim 26 wherein the step of generating the slope of said calibration flow rate curve include the step of mathematically processing the periodic flow path pressure measurements to obtain a Binomial fit having a linear portion attributable to the slope.

28. The method of controlling according to claim 13 wherein the step of generating a control curve includes the step of utilizing a predetermined pressure offset that is between the zero-flow rate pressure point and the cuff pressure.

29. The method of controlling according to claim 28 wherein the step of generating a control curve includes the step of utilizing a predetermined pressure offset that is equal to a fraction of the cuff pressure.

30. The method of controlling according to claim 29 wherein the step of generating a control curve includes the step of utilizing a predetermined pressure that is equal to one-quarter the cuff pressure.

31. The method of controlling according to claim 13 wherein the step of making periodic flow path measurements includes the step of rapidly and uniformly accelerating and decelerating pumping of the fluid from the subject so that a plurality of pressure measurements can be taken periodically.

32. The method of claim 13 further comprising the steps of inflating the pressure cuff to pressurize the subject's blood vessel prior to venipuncture, initiating the venipuncture and deflating the pressure cuff prior to sensing the internal fluid pressure within the subject's blood vessel.

33. A system for calibrating the control of the flow of fluid in a given direction to or from a subject having a limited flow rate accommodation comprising:

a pressure cuff coupled to the subject to provide pressurization of the subject's blood vessel to increase the dynamic range of operating internal vein pressures;

a fluid pump that is connectable in fluid pumping relationship along a fluid flow path between the subject and a fluid processor or reservoir;

pressure sensing means coupled to sense fluid pressure in the fluid flow path between the fluid pump and the subject and generate indications of the sensed pressure;

a flow rate sensor coupled to provide an indications of fluid flow rates along the first fluid flow path; and a fluid pump control system coupled to receive the sensed pressure and flow rate indications and provide to the fluid pump flow rate control signals in response thereto, the fluid pump control system including:

(a) means for inflating and deflating the pressure cuff;

(b) means for generating a zero-flow point, including means for sensing the internal fluid pressure within the subject's blood pressure at a zero flow rate while the pressure cuff is deflated, said zero flow point being an indication of pressure within the subject at zero flow rate;

(c) means for generating a calibration flow rate curve including means for rapidly and uniformly accelerating said fluid pump while the pressure cuff is inflated so that a plurality of flow path pressure measurements can be taken periodically;

(d) means for generating a flow rate control curve utilizing the slope of said calibration flow rate curve, said zero-flow point, and a translation from said zero-flow point corresponding to a predetermined intravascular pressure value; and (e) means for generating during conditions of normal operation flow rate control signals limiting the actual flow rate to a magnitude along the flow rate control curve.

34. The system of claim 33 wherein said means for generating a calibration flow rate curve includes means for mathematically processing the periodic flow path pressure measurements to obtain a Least-Squares slope estimation.

35. The system of claim 33 wherein said means for generating a calibration flow rate curve includes means for adjusting the slope of said calibration flow rate curve to correct for changes in internal vein pressure during the calibration period.

36. The system of claim 33 wherein said means for generating a calibration flow rate curve include means for mathematically processing the periodic flow path pressure measurements to obtain a Binomial fit having a linear portion attributable to the slope.

37. The system of claim 33 wherein said means for inflating and deflating the pressure cuff further comprises means for inflating the pressure cuff to pressurize the subject's blood vessel prior to venipuncture.

38. A system for calibrating the control of the flow of fluid in a given direction to or from a subject having a limited flow rate accommodation comprising:

a pressure cuff coupled to the subject to provide pressurization of the subject's blood vessel to increase the dynamic range of operating internal vein pressures;

a fluid pump that is connectable in fluid pumping relationship along a fluid flow path between the subject and a fluid processor or reservoir;

pressure sensing means coupled to sense fluid pressure in the fluid flow path between the fluid pump and the subject and generate indications of the sensed pressure;

a flow rate sensor coupled to provide an indications of fluid flow rates along the first fluid flow path; and a fluid pump control system coupled to receive the sensed pressure and flow rate indications and provide to the fluid pump flow rate control signals in response thereto, the fluid pump control system including:

(a) means for inflating and deflating the pressure cuff;

(b) means for generating a zero-flow point, including means for sensing the internal fluid pressure within the subject's blood pressure at a zero flow rate while the pressure cuff is deflated, said zero flow point being an indication of pressure within the subject at zero flow rate;

(c) means for generating a calibration flow rate curve including means for rapidly and uniformly accelerating and decelerating said fluid pump while the pressure cuff is inflated so that a plurality of flow path pressure measurements can be taken periodically;

(d) means for generating a flow rate control curve utilizing the slope of said calibration flow rate curve, said zero-flow point, and a translation from said zero-flow point corresponding to a predetermined intravascular pressure value; and (e) means for generating during conditions of normal operation flow rate control signals limiting the actual flow rate to a magnitude along the flow rate control curve.

39. The system of claim 38 wherein said means for generating a calibration flow rate curve includes means for mathematically processing the periodic flow path pressure measurements to obtain a Least-Squares slope estimation.

40. The system of claim 38 wherein said means for generating a calibration flow rate curve includes means for adjusting the slope of said calibration flow rate curve to correct for changes in internal vein pressure during the calibration period.

41. The system of claim 38 wherein said means for generating a calibration flow rate curve include means for mathematically processing the periodic flow path pressure measurements to obtain a Binomial fit having a linear portion attributable to the slope.

42. The system of claim 38 wherein said means for inflating and deflating the pressure cuff further comprises means for inflating the pressure cuff to pressurize the subject's blood vessel prior to venipuncture.

* * * * *